United States Patent [19]
Huang et al.

[11] Patent Number: 5,639,465
[45] Date of Patent: Jun. 17, 1997

[54] STABILIZED THIOCARBAMATE HERBICIDES

[75] Inventors: Candice W. Huang; Kang-Chi Lin, both of Lafayette, Calif.

[73] Assignee: Zeneca Limited, London, United Kingdom

[21] Appl. No.: 518,661

[22] Filed: Aug. 24, 1995

Related U.S. Application Data

[63] Continuation of Ser. No. 210,206, Mar. 17, 1994, abandoned, continuation-in-part of Ser. No. 93,374, Jul. 19, 1993, abandoned.

[51] Int. Cl.$^6$ .................................................. A01N 25/12
[52] U.S. Cl. .......................... 424/409; 424/405; 424/408; 424/420; 424/421
[58] Field of Search ................................. 424/405, 409, 424/420, 421, 408

[56] References Cited

U.S. PATENT DOCUMENTS

| | | |
|---|---|---|
| 3,198,786 | 8/1965 | Tilles . |
| 3,877,927 | 4/1975 | Martin . |
| 4,313,941 | 2/1982 | Duinker et al. . |
| 4,398,238 | 8/1983 | Kaufman . |
| 4,400,199 | 8/1983 | Yokoyama et al. . |
| 4,485,103 | 11/1984 | Pasareza ................. 424/202 |
| 4,878,941 | 11/1989 | Theodoridis ................ 71/93 |
| 5,139,774 | 8/1992 | Meinard et al. .......... 514/521 |
| 5,230,892 | 7/1993 | Gotou et al. .............. 424/409 |

OTHER PUBLICATIONS

Grim, Ralph E., "Clay Mineralogy", (McGraw-Hill, NY, 1968), p. 34 Cite Publication Pesticide Solid Diluents and Carriers (Middleport NY, 1979).
Yaffe, J. Agr. Food Chem. 6, 903 (1958).
Fowkes et al., J. Agr. Food Chyem. 8, 203 (1960).

*Primary Examiner*—Neil S. Levy
*Attorney, Agent, or Firm*—Joel G. Ackerman; Joseph R. Snyder

[57] ABSTRACT

This invention comprises a granular pesticidal composition having improved attrition resistance comprising from about 10 to about 20% by weight of a pesticide, a glycol or polyvinyl alcohol, the remainder comprising montmorillonite or kaolin clay granules.

17 Claims, No Drawings

STABILIZED THIOCARBAMATE HERBICIDES

This application is a continuation of application Ser. No. 08/210,206, filed Mar. 17, 1994, now abandoned, which is a continuation-in-part of application Ser. No. 08/093,374, filed Jul. 19, 1993, now abandoned.

This invention relates to granular pesticidal compositions, which are particularly suitable for use in aerial application of pesticides and are characterized by a comparatively low attrition rate.

As background, a commercially available formulation of molinate herbicide used for aerial application to control weeds in rice paddies contains 10 to 15 weight percent molinate supported on kaolin clay granules. Such formulations have a resistance to attrition of between about 82.5 to 83.5%, as measured by ASTM Standard E 728-86. Between about 16.5 to 17.5% of the material passes through a 40 mesh sieve. It would be desirable to produce a product with higher attrition resistance and correspondingly less dust formation resulting from normal handling including bagging, shipping and loading. Such a product would have improved qualities in terms of less worker exposure hazard to the pesticide due to the formation of smaller amounts of dust.

One possible expedient would be to utilize a clay support which in and of itself has a higher resistance to attrition than kaolin. One such support is montmorillonite clay, which does tend to have a higher resistance to attrition than kaolin. Montmorillonite clay is used in some pesticidal formulations, for instance, ERADICANE 25G herbicide, which is a pesticide containing the herbicide EPTC plus an herbicide safener, and which is applied directly into the soil for pre-emergence control of weeds in corn.

However, utilization of a montmorillonite-supported formulation for aerial application is problematic because the montmorillonite particles have a substantially lower bulk density than kaolin and thus would be more susceptible to drift. Additionally, the montmorillonite particles would have a greater tendency to float on the surface of water as opposed to sinking, which would adversely affect the distribution of the pesticide into the water.

Surprisingly, it has been found that the inclusion of a glycol, particularly dipropylene glycol, or polyvinyl alcohol into a kaolin- or montmorillonite-supported granular pesticidal composition produces granules which have a sufficient bulk density for aerial application and, in addition, an unusually and unexpectedly enhanced attrition resistance.

SUMMARY OF THE INVENTION

This invention comprises a granular pesticidal composition supported on kaolin or on montmorillonite clay, comprising (a) from about 10 to about 20%, preferably from about 10 to about 15%, by weight of a pesticide;

(b) a component selected from
   (i) one or more of ethylene glycol, diethylene glycol, propylene glycol or dipropylene glycol, or
   (ii) polyvinyl alcohol;

the remainder comprising kaolin or montmorillonite clay, and wherein:

the composition contains from about 2.5 to about 5% by weight glycol or from about 1 to about 2% by weight polyvinyl alcohol if the support is kaolin, and from about 8 to about 15% by weight glycol or from about 1 to about 4% by weight polyvinyl alcohol if the support is montmorillonite.

DETAILED DESCRIPTION OF THE INVENTION

Compositions of this type may contain any suitable pesticide, and particularly pesticides which would be applied for control of weeds in paddy rice. Such pesticides would include thiocarbamates such as molinate and other suitable pesticides such as propanil, thiobencarb, pendimethalin, fenoxaprop-ethyl, quinchlorac and acifluorfen. One class of pesticides usable in the compositions of this invention are those whose destabilization or decomposition is not accelerated by kaolin or montmorillonite clays used as granular supports, such as certain organophosphorus insecticides. In a preferred embodiment, this invention comprises such granules containing a thiocarbamate herbicide and in a most preferred embodiment, molinate.

If a glycol is utilized, compositions according to this invention will contain from about 2.5 to about 5 weight percent glycol of the support in kaolin. If the support is montmorillonite, the compositions will contain from about 8 to about 15, preferably from about 10 to about 15 and most preferably from greater than 10 to about 15, weight percent glycol. The preferred glycol is dipropylene glycol. A mixture of two or more glycols may be used.

Glycols are incorporated into the compositions by conventional techniques, such as spraying.

Polyvinyl alcohol is a solid and must be dissolved in water to be incorporated into the compositions. In general, such solutions contain maximum 24% polyvinyl alcohol. The polyvinyl alcohol is also incorporated into the compositions by spraying. Kaolin-supported compositions will contain from about 1 to about 2 weight percent polyvinyl alcohol; montmorillonite-supported compositions, from about 1 to about 4 weight percent.

In addition, compositions according to this invention may contain various additives or adjuvants as necessary or advantageous.

Tests have also determined that sometimes the particle size of the montmorillonite granules can have an affect on the attrition resistance of compositions according to this invention. In particular, it was found that pesticidal compositions containing 10 or 15 weight percent molinate together with 10 weight percent dipropylene glycol supported on smaller montmorillonite particles (14/24 and 16/30 mesh, respectively) did not demonstrate improved attrition resistance as compared with kaolin granules containing 15% molinate. On the other hand, compositions containing 10 weight percent molinate and 15 weight percent dipropylene glycol supported on such smaller particles of montmorillonite did show improved attrition resistance. Consequently, it appears that higher amounts of glycol are needed for smaller particle-sized supports.

Another advantage demonstrated by some of the compositions of this invention supported on montmorillonite is decreased vaporization of molinate on heating the compositions. This might have been expected, however, from the fact that montmorillonite has a higher absorbability than kaolin (30–35% as opposed to 17% liquid capacity). Nevertheless, this provides an additional advantage in lowering exposure to the pesticides when contained in compositions according to the present invention.

Attrition Resistance

Attrition resistance was measured using ASTM Standard E 728-86.

Bulk density was measured using ASTM Standard E 727-86.

Headspace content was measured as follows:

One gram of the granules to be tested was sealed in a vial which was then heated at 50° C. for 3 hours. The molinate content of the headspace (space in the vial above the granular material) was assayed using a gas chromatographic headspace analyzer. Molinate content was determined with respect to pure reference standards representing 100% saturation, as a control.

The Table shows the results of these tests for compositions variously supported on kaolin and three different sizes of montmorillonite granules.

The kaolin granules were size 16/40, Little Rock Kaolin, obtained from Geo Specialty Chemicals. The montmorillonite granules were as indicated size 8/16, 14/24 or 16/30 mesh obtained from Oil-Dri Corporation of America.

The Table shows the comparison of results obtained by testing compositions on montmorillonite or kaolin supports, as compared to the prior art molinate compositions supported on kaolin granules without added glycol or polyvinyl alcohol as well as molinate supported on montmorillonite without these materials (which composition is not in the prior art). As can be seen, the compositions according to this invention generally demonstrated superior resistance to attrition. The only compositions which did not demonstrate this advantage were those containing 10 and 15 weight percent molinate plus 10 weight percent dipropylene glycol supported on smaller (14/24 and 16/30 mesh, respectively) montmorillonite granules. These demonstrated approximately the same attrition resistance as kaolin granules containing 15 weight percent molinate.

b) a component selected from one or more of ethylene glycol, diethylene glycol, propylene glycol or dipropylene glycol;

the remainder comprising kaolin or montmorillonite clay, and wherein:

the composition contains from about 2.5 to about 5% by weight glycol if the support is kaolin, and from about 8 to about 15% by weight glycol if the support is montmorillonite.

2. A composition according to claim 1 in which the pesticide is one whose destabilization or decomposition is not accelerated by kaolin or montmorillonite.

3. A composition according to claim 1 in which the pesticide is a herbicide suitable for controlling weeds in rice crops.

4. A composition according to claim 3 in which the pesticide is molinate.

5. A composition according to claim 1 in which the support is montmorillonite.

6. A composition according to claim 5 in which component (b) is dipropylene glycol.

7. A composition according to claim 6 containing from about 10 to about 15 weight percent dipropylene glycol.

8. A composition according to claim 6 in which the montmorillonite clay granules are minimum size 8/16 mesh.

9. A composition according to claim 6 having a resistance to attrition of at least about 86 percent.

10. A composition according to claim 5 in which component (b) is ethylene glycol.

11. A composition according to claim 1 in which the support is kaolin and component (b) is dipropylene glycol.

TABLE

| Support | Size | Wt/% Molinate | Wt/% of Indicated Component | Attrition Resistance % | Headspace % | Bulk Density lb/cu. ft. |
| --- | --- | --- | --- | --- | --- | --- |
| Kaolin | 16/40 | 10 | — | 83.4 | 82.4 | 52.3 |
| Kaolin | 16/40 | 15 | — | 82.7 | 89.9 | 56.5 |
| Montmorillonite | 8/16 | 10 | — | 89.7 | — | 43.9 |
| Montmorillonite | 8/16 | 15 | — | 87.3 | — | 46.6 |
| DIPROPYLENE GLYCOL | | | | | | |
| Montmorillonite | 8/16 | 10 | 10 | 95.4 | 67.2 | 45.3 |
| Montmorillonite | 8/16 | 10 | 15 | 98.5 | 72.6 | 47.9 |
| Montmorillonite | 8/16 | 15 | 10 | 97.6 | 76.00 | 47.7 |
| Montmorillonite | 14/24 | 10 | 10 | 81.4 | 66.9 | 42.1 |
| Montmorillonite | 14/24 | 10 | 15 | 86.4 | 72.1 | 43.4 |
| Montmorillonite | 14/24 | 15 | 10 | 81.8 | 73.5 | 43.8 |
| Montmorillonite | 16/30 | 10 | 10 | 82.2 | 60.4 | 43.1 |
| Montmorillonite | 16/30 | 10 | 15 | 86.8 | 65.0 | 45.1 |
| Montmorillonite | 16/30 | 15 | 10 | 82.0 | 75.4 | 44.8 |
| Kaolin | 16/40 | 10 | 5 | 88.4 | 72.0 | 56.3 |
| Kaolin | 16/40 | 15 | 2.5 | 90.9 | 89.9 | 58.5 |
| ETHYLENE GLYCOL | | | | | | |
| Montmorillonite | 8/16 | 10 | 10 | 85.2 | — | 43.8 |
| Montmorillonite | 8/16 | 10 | 15 | 88.4 | — | 46.1 |
| POLYVINYL ALCOHOL | | | | | | |
| Montmorillonite | 8/16 | 10 | 1 | 92.4 | 56.5 | 35.9 |
| Montmorillonite | 8/16 | 15 | 1 | 93.1 | 74.1 | 37.3 |

What is claimed is:

1. A granular pesticidal composition supported on kaolin or on montmorillonite clay, suitable for aerial application, comprising a) from about 10 to about 20% by weight of a thiocarbamate herbicide pesticide;

12. A composition according to claim 1 containing from about 10 to about 15 weight percent pesticide.

13. A composition according to claim 1 comprising from about 10 to about 15 weight percent molinate; from about 10 to about 15 weight percent dipropylene glycol, the remainder comprising montmorillonite clay granules having a minimum size of 8/16 mesh.

14. A method for controlling weeds in rice crops comprising applying to a rice crop or the locus thereof a composition according to claim 1.

15. A method according to claim 14 in which the support is montmorillonite.

16. A method according to claim 14 in which the composition is applied to paddy rice by aerial application.

17. A method according to claim 15 in which the composition is applied to paddy rice by aerial application.

* * * * *